US012426845B2

(12) United States Patent
Tetsumura et al.

(10) Patent No.: US 12,426,845 B2
(45) Date of Patent: Sep. 30, 2025

(54) X-RAY CT APPARATUS, IMAGE PROCESSING APPARATUS, AND MOTION-CORRECTED IMAGE RECONSTRUCTION METHOD

(71) Applicant: FUJIFILM Healthcare Corporation, Kashiwa (JP)

(72) Inventors: Yusuke Tetsumura, Chiba (JP); Ryota Kohara, Chiba (JP); Yuta Ogura, Chiba (JP); Yoshiki Mori, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 348 days.

(21) Appl. No.: 18/131,181

(22) Filed: Apr. 5, 2023

(65) Prior Publication Data

US 2023/0329662 A1    Oct. 19, 2023

(30) Foreign Application Priority Data

Apr. 13, 2022   (JP) ................. 2022-066503

(51) Int. Cl.
*A61B 6/00*   (2024.01)
*A61B 6/03*   (2006.01)
*G06T 7/246*  (2017.01)
*G06T 11/00*  (2006.01)

(52) U.S. Cl.
CPC ............ *A61B 6/527* (2013.01); *A61B 6/032* (2013.01); *A61B 6/541* (2013.01); *G06T 7/248* (2017.01); *G06T 11/005* (2013.01); *G06T 2207/10081* (2013.01); *G06T 2207/30048* (2013.01); *G06T 2210/41* (2013.01)

(58) Field of Classification Search
CPC ......... A61B 6/527; A61B 6/032; A61B 6/541; A61B 6/5205; A61B 6/5264; A61B 6/4411; A61B 6/503; A61B 6/5258; G06T 7/248; G06T 11/005; G06T 2207/10081; G06T 2207/30048; G06T 2210/41
See application file for complete search history.

(56) References Cited

U.S. PATENT DOCUMENTS

| | | | |
|---|---|---|---|
| 7,783,001 B2 * | 8/2010 | Hagiwara ............. | G06T 11/006 378/20 |
| 10,165,989 B2 * | 1/2019 | Seo ...................... | A61B 6/5258 |
| 10,398,392 B2 * | 9/2019 | Suzuki ................ | A61B 6/5205 |
| 2018/0110480 A1 * | 4/2018 | Suzuki ................ | G06T 1/0007 |

* cited by examiner

*Primary Examiner* — Tom Y Lu
(74) *Attorney, Agent, or Firm* — Paul Teng

(57) ABSTRACT

When motion information of a subject during scanning is acquired from an image pair and motion-corrected image reconstruction is performed to generate a CT image, erroneous recognition and excessive smoothing of a motion component are prevented, and the accuracy of motion correction is improved. A filtering unit for reducing noise of the image pair is provided. The filtering unit acquires a relation between indicators for noise amounts acquired based on information that affects noise amounts of a first image and a second image constituting the image pair, and adjusts smoothness of each image using the relation between the indicators. The presence or absence of a motion is determined for the image pair subjected to noise reduction by filtering, normalization degrees of the two images are made different according to the presence or absence of the motion and the two images are normalized, and the magnitude and a direction of the motion are detected.

11 Claims, 14 Drawing Sheets

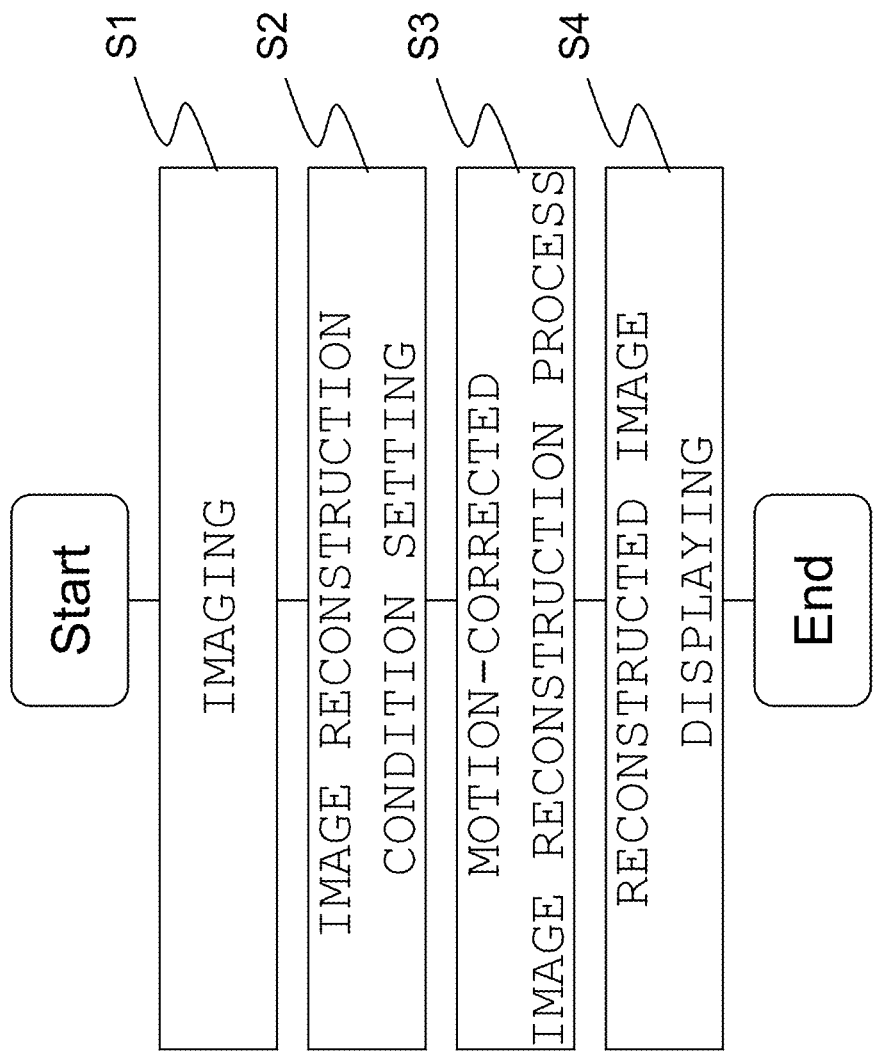

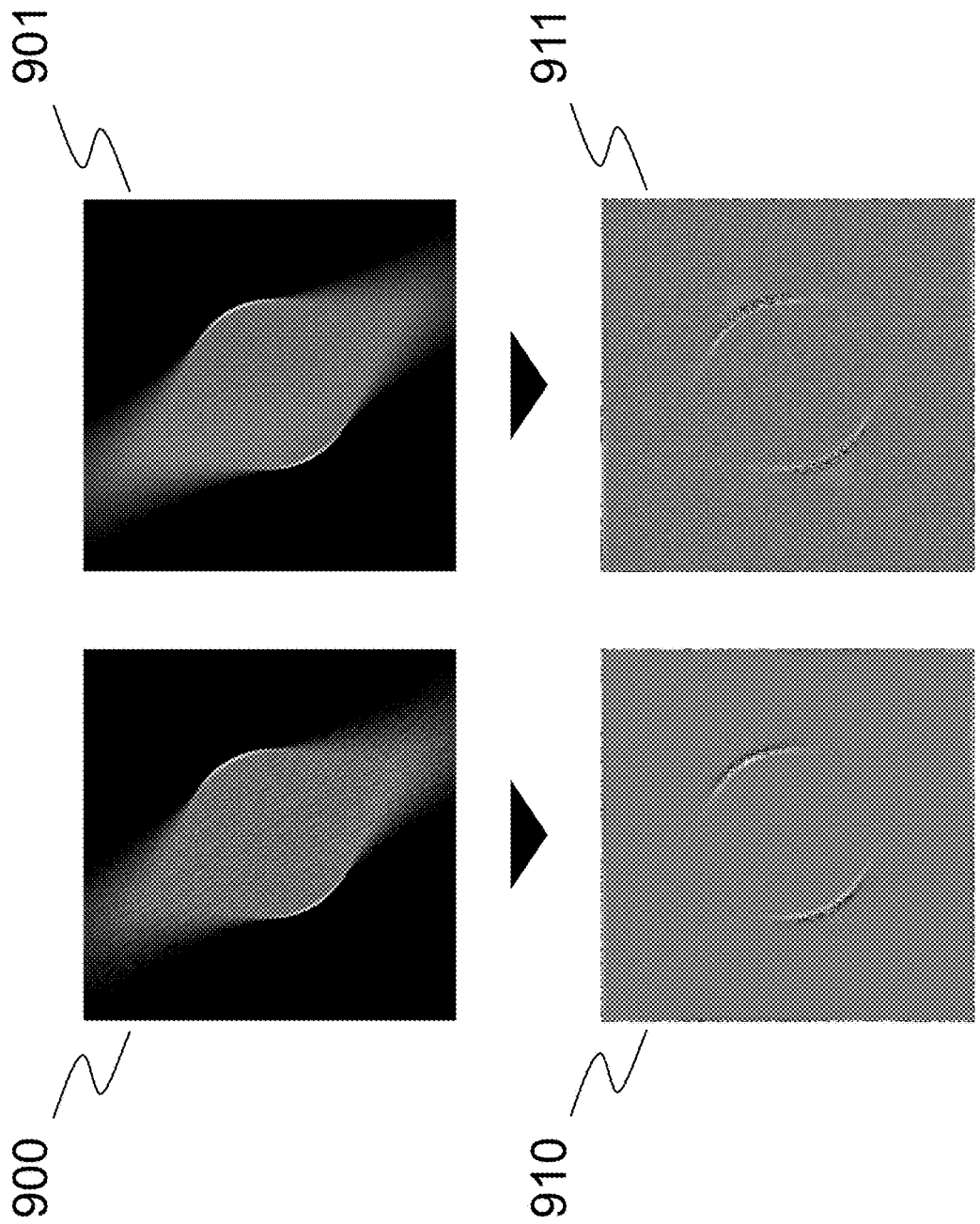

X-RAY CT APPARATUS, IMAGE PROCESSING APPARATUS, AND MOTION-CORRECTED IMAGE RECONSTRUCTION METHOD

BACKGROUND OF THE INVENTION

1. Field of the Invention

The present invention relates to an X-ray CT apparatus that irradiates a subject with X-rays to acquire a medical image, and relates to a motion-corrected image reconstruction processing technique for improving image interpretation accuracy and image interpretation efficiency for a subject having a motion.

2. Related Art

In a CT examination for a subject having a motion such as the heart, a motion artifact may occur in an image due to the subject moving during a CT scan. A quality of the image decreases due to the motion artifact, and as a result, diagnostic accuracy and diagnostic efficiency for a disease by a doctor, a medical technologist, or the like (hereinafter, collectively referred to as an examiner) may be reduced. Therefore, a motion-corrected image reconstruction process for reducing the motion artifact occurred in a CT image of the subject having a motion is performed.

In the motion-corrected image reconstruction process, the motion of the subject is estimated based on a pair of images (a first image and a second image) temporally reconstructed at positions directly facing each other with a target image reconstruction position as a center, and reconstruction is performed by performing back projection while correcting an image of the target reconstruction position using information on the estimated motion. Here, when noise is included in the two images used for estimation of the motion, there is a problem that the noise is erroneously recognized as a motion, a motion buried in the noise cannot be detected, or the like. Therefore, it is important to accurately extract the motion of the subject from the first image and the second image including the noise.

U.S. Pat. No. 10,165,989B (PTL 1) discloses a method of extracting only a motion of a subject by performing a noise reduction process for a first image and a second image. In the method disclosed in PTL 1, the noise reduction to which a low-pass filter is applied is performed based on an X-ray dose when the first image and the second image are acquired.

CITATION LIST

Patent Literature

PTL 1: U.S. Pat. No. 10,165,989B

SUMMARY OF THE INVENTION

According to the method disclosed in PTL 1, although the noise is reduced according to noise of each of the first image and the second image, a relation of noise between the images is not considered. Therefore, a difference in noise between the two images may be erroneously recognized as a motion component, and the motion component may be lost due to excessive smoothing. In such a case, a motion correction effect is impaired. In addition, since motion correction in the related art is performed without considering whether the subject is moving currently, when the motion correction is performed for the subject having a fairly small motion, an unnatural distortion may occur in an image.

Accordingly, an object of the invention is to prevent the erroneous recognition and the excessive smoothing of the motion component described above, and improve the accuracy of the motion correction.

In order to solve the above problems, the invention prevents a decrease in the motion correction effect by determining a smoothing parameter of a filter in consideration of a relation between noise amounts of the pair of images, that is, the first image and the second image used for the motion correction, and applying the smoothing parameter to the images.

That is, an X-ray CT apparatus according to the invention includes an imaging unit provided with an X-ray source and an X-ray detector which rotate around a subject, and configured to acquire transmitted X-ray data of the subject in a predetermined angle range, an image reconstructing unit configured to generate a reconstructed image using the transmitted X-ray data acquired by the imaging unit, and an image processing unit. Further, the image processing unit includes an image pair generating unit configured to generate an image pair at positions directly facing each other using a part of the transmitted X-ray data, a noise reducing unit configured to perform noise reduction for each image of the image pair generated by the image pair generating unit, and a motion information acquiring unit configured to acquire motion information of the subject during scanning using the image pair after the noise reduction. The noise reducing unit performs, based on a relation between indicators for noise amounts of the images included in the image pair, the noise reduction for each image of the image pair, and the image reconstructing unit generates a reconstructed image by correcting a motion of the subject during scanning using the motion information calculated by the motion information acquiring unit.

The indicator for the noise amount is an indicator indicating a noise amount to be obtained based on various conditions that affect a noise amount of an image in imaging.

An image processing apparatus according to the invention is an image processing apparatus that processes the transmitted X-ray data collected by the X-ray CT apparatus, and has a function similar to that of the image processing unit of the X-ray CT apparatus described above.

Further, a motion-corrected image reconstruction method according to the invention is a method for correcting a motion of a subject during scanning using transmitted X-ray data and reconstructing a CT image. The method includes: generating an image pair using a part of the transmitted X-ray data; performing noise reduction for each image of the image pair, and at that time, adjusting, based on a relation between indicators for noise amounts of the images included in the image pair, filtering smoothness at a time of the noise reduction; acquiring motion information of the subject from the image pair after the noise reduction; and reconstructing an image using the motion information and the transmitted X-ray data.

The noise reduction process can be performed in which loss of the motion information is minimized for the first image and the second image, and the motion correction effect can be maximized. In addition, it is possible to adjust a motion intensity based on the presence or absence of the motion of the subject, and it is possible to prevent the occurrence of false deformation in the corrected image due to image noise. As a result, it is possible to improve diagnostic accuracy and diagnostic efficiency for a disease by a user.

BRIEF DESCRIPTION OF THE DRAWINGS

FIG. 3A is a diagram illustrating a flow of imaging including motion-corrected image reconstruction.

FIG. 9 is a diagram illustrating an example of a result of a filtering process according to the first embodiment.

DESCRIPTION OF THE PREFERRED EMBODIMENTS

Hereinafter, embodiments of the invention will be described with reference to the drawings.

First, an overall configuration of an X-ray CT apparatus to which the invention is applied will be described.

Figure 1:
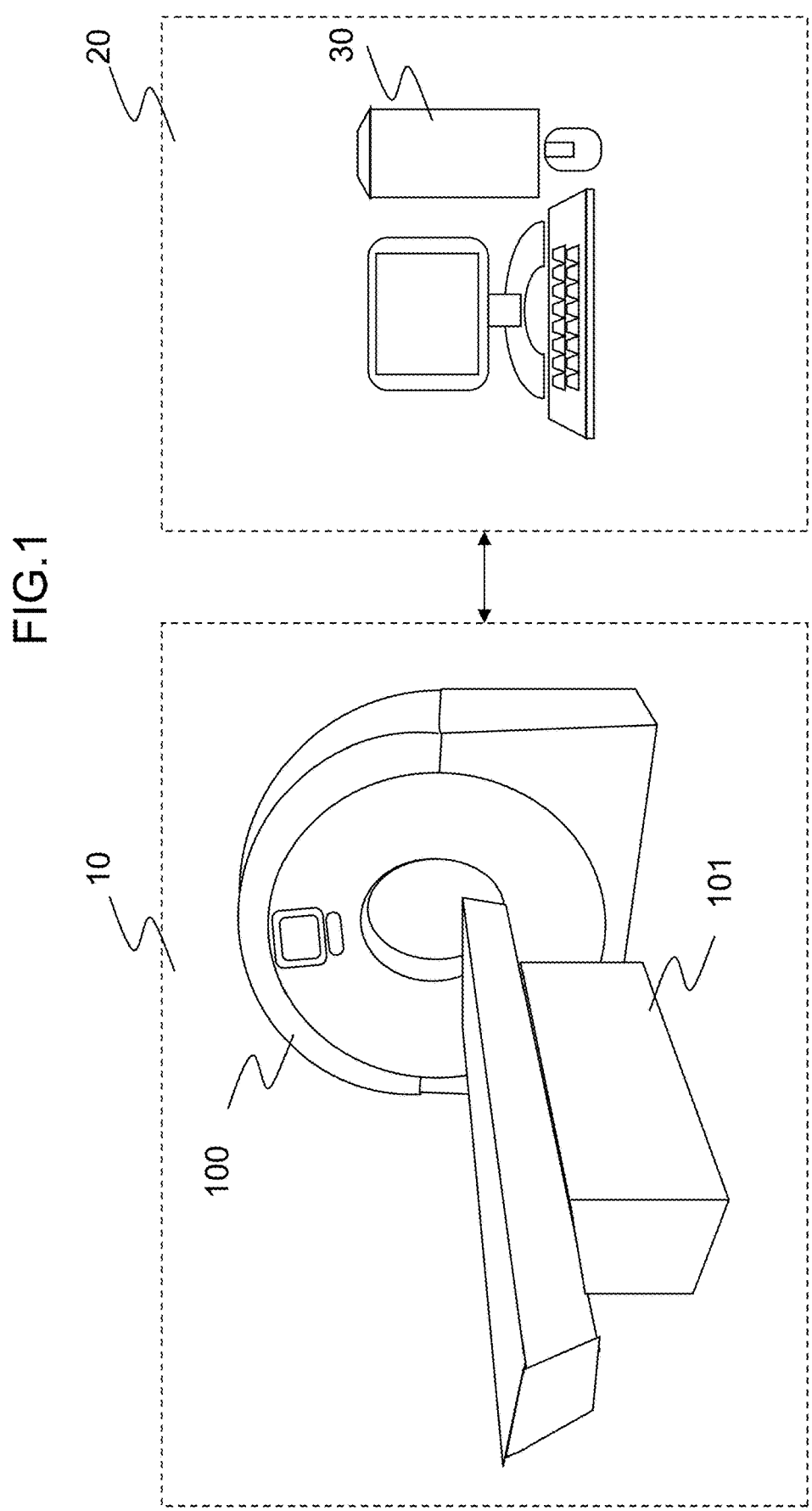
FIG. 1 is a diagram illustrating an overall configuration of an X-ray CT apparatus according to the invention.

As illustrated in FIG. 1, an X-ray CT apparatus 1 includes an imaging unit 10 that includes a gantry 100 for capturing a tomographic image and a fluoroscopic image of a subject 3 and a bed device 101, and an operating unit 20 that operates and controls the imaging unit 10.

Figure 2:
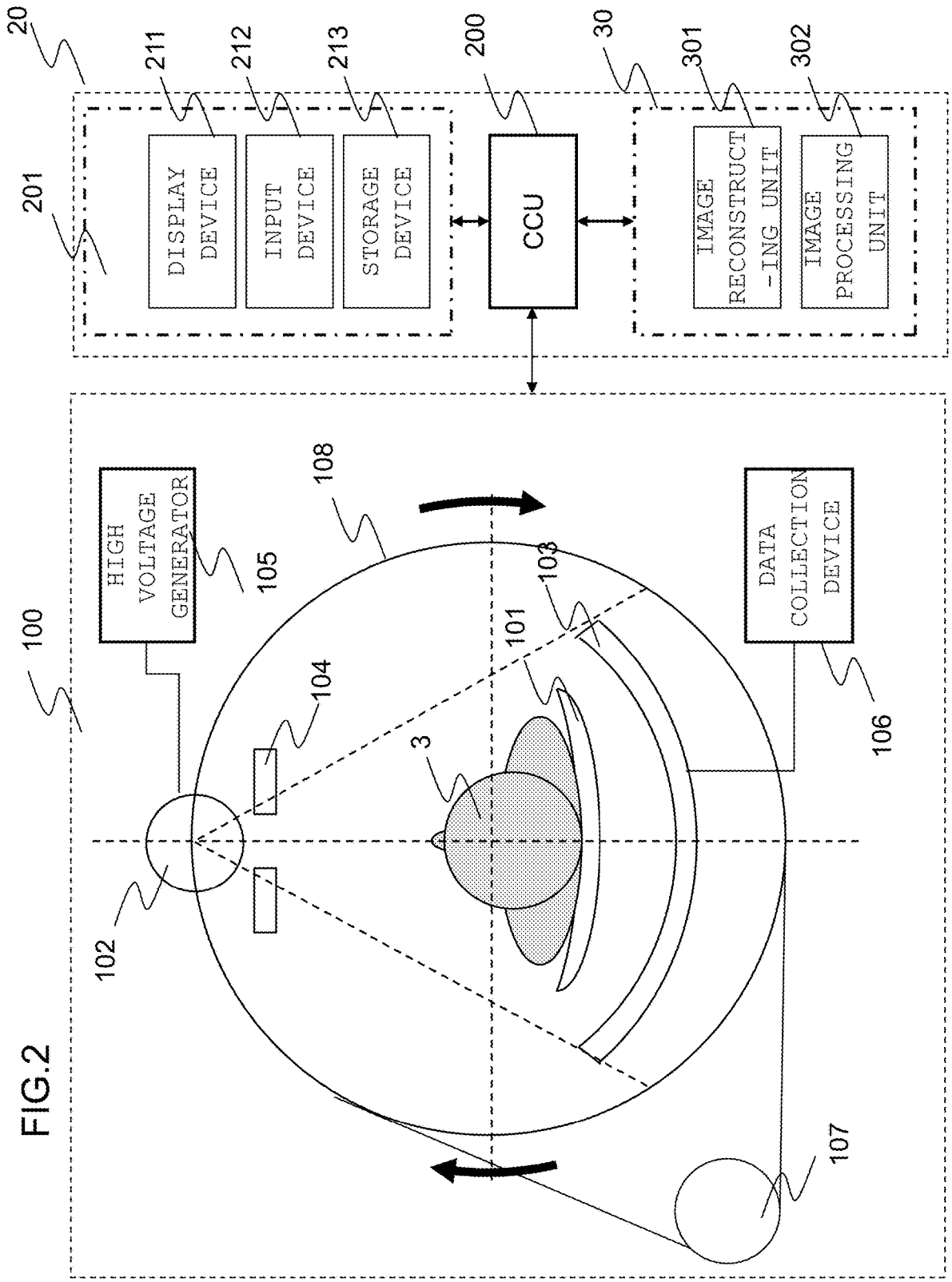
FIG. 2 is a diagram illustrating elements of the X-ray CT apparatus according to the invention.

As illustrated in FIG. 2, the gantry 100 is provided with an X-ray generator 102 that generates X-rays with which the subject 3 is irradiated, collimator devices 104 that narrow a beam of X-rays generated by the X-ray generator 102, an X-ray detector 103 that detects X-rays transmitted through the subject, a scanner 108 that is mounted with the above, a high voltage generator 105 that applies a high voltage to the X-ray generator 102, a data collection device 106 that collects transmitted X-ray data acquired from the X-ray detector 103, and a driving device 107 that rotates the scanner around the subject 3. The X-ray generator 102 includes an X-ray tube (not illustrated). A predetermined tube current flows through the X-ray tube, so that the subject 3 is irradiated with a predetermined dose of X-rays.

The operating unit 20 includes a central control unit 200 that controls devices built in the gantry, and an input and output device 210 that functions as a user interface for communicating between a user and the central control unit 200. A calculating unit 30 that performs various calculations such as image reconstruction for the transmitted X-ray data collected by the data collection device 106 is mounted within the central control unit 200. Alternatively, a calculation unit different from the central control unit 200 may be provided, and such a calculation unit may function as the calculating unit 30. A function of the central control unit 200 is achieved by the central control unit 200 reading and executing a program describing a calculation algorithm or a processing procedure of a control. Alternatively, a part of a calculation operation or a process to be performed by the calculating unit 30 may also be performed using a programmable logic device (PLD) such as an ASIC or an FPGA.

The input and output device 210 includes an input device 212 that is used to input an imaging condition and the like by an operator, a display device 211 that displays data such as a captured image or a GUI, and a storage device 213 that stores a program and data required for imaging such as a device parameter.

The calculating unit 30 includes an image reconstructing unit 301 that performs a back projection process for the transmitted X-ray data acquired by the data collection device 106 to create a tomographic image, and an image processing unit 302 that performs analysis of image data, image correction, and the like. The image correction includes motion-corrected image reconstruction. The details thereof will be described later.

The central control unit 200 controls, according to an operation instruction from the operator via the input device 212, the imaging unit 10 (the X-ray generator 102, the X-ray detector 103, the high voltage generator 105, the collimator devices 104, the bed device 101, the driving device 107, and the data collection device 106), the input and output device 210, and the calculating unit 30. Under control performed by the central control unit 200, these units operate, and reconstruction of a CT image, correction of a reconstructed CT image, and the like are performed.

An outline of an operation of the X-ray CT apparatus to be performed under the control performed by the central control unit 200 will be described with reference to flows in FIGS. 3A and 3B.

Step S1

The subject 3 is placed on the bed device 101 and localization scan is performed. The localization scan is imaging for setting an imaging range of the subject 3, and a transmitted X-ray image is acquired along a body axis direction while changing relative positions of the scanner 108 and the bed device 101 (the subject 3). An examiner sets the imaging range using the transmitted X-ray image. Next, the imaging unit 10 performs tomography accompanying rotation of the scanner 108 within an imaging range set based on the localization scan image, and collects transmitted X-ray data of the subject.

Step S2

An image reconstruction condition for the transmitted X-ray data of the subject acquired in the imaging step S1 is set. The image reconstruction condition is, for example, a thickness of an image (a thickness of a cross section), an FOV, a condition for a filter, and the like, and further includes settings such as a reconstruction cardiac phase (a target reconstruction cardiac phase: which cardiac phase image is to be reconstructed) in a case of electrocardiogram gated imaging. In the electrocardiogram gated imaging, a target image reconstruction position is determined by setting the target reconstruction cardiac phase. The image processing unit 302 receives these image reconstruction conditions set by a user via the input device 212.

Step S3

The image processing unit 302 performs, based on the image reconstruction conditions set in the condition setting step S2, image reconstruction using the transmitted X-ray data of the subject acquired in the imaging step S1. At this time, motion information of the subject during the imaging is acquired, and an image is reconstructed by correcting a motion (the motion-corrected image reconstruction).

Figure 3B:
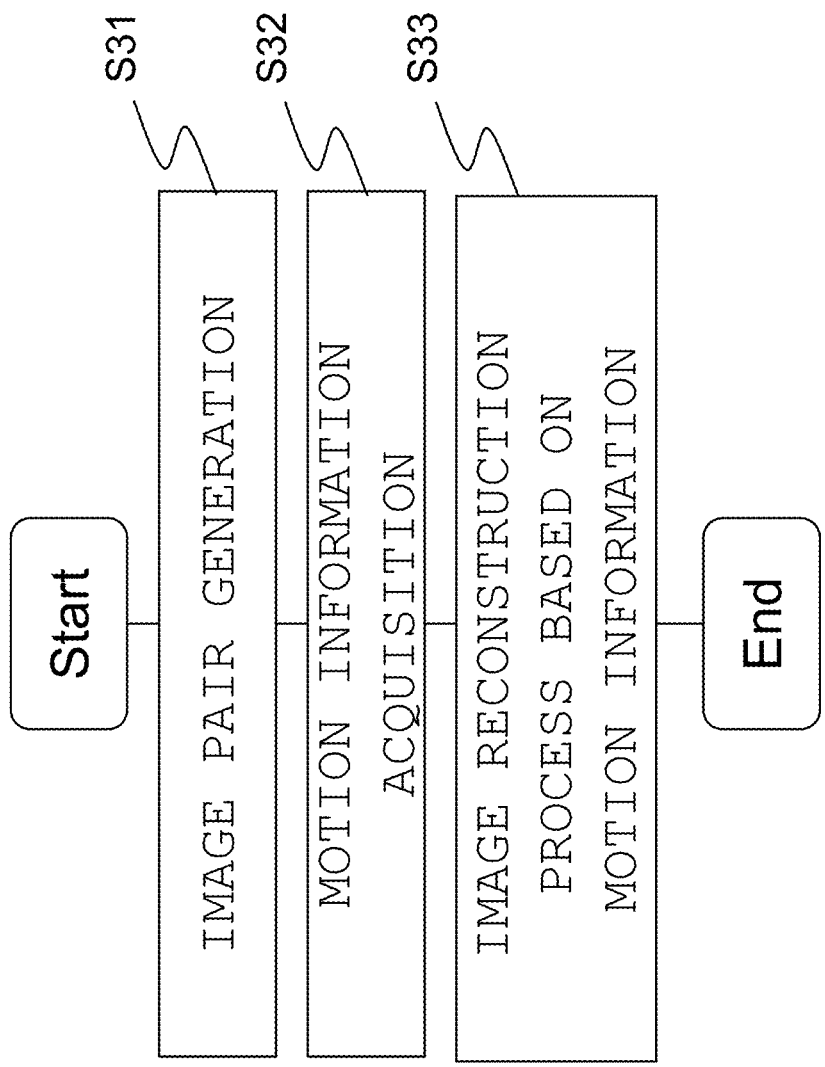
FIG. 3B is a diagram illustrating a flow of a motion-corrected image reconstruction process.

As illustrated in FIG. 3B, the motion-corrected image reconstruction step S3 includes a step (an image pair generation step) S31 of generating a pair of images (an image pair) used for detecting a motion based on the transmitted X-ray data collected in the imaging step S1, a step (a motion information acquisition step) S32 of detecting a motion using the image pair, and a step (a reconstruction step) S33 of performing image reconstruction using the transmitted X-ray data collected in the imaging step S1 and the motion information detected in step S32. In the image pair generation step S31, a process (filtering) of reducing noise for a first image and a second image that constitute the image pair is performed. The details of these processes will be described later.

Step S4

Finally, motion-corrected image data created in the reconstruction step S3 is displayed on the display device 211.

A CT image in which a motion is corrected is acquired in the above steps S1 to S4 and is presented to the examiner. Hereinafter, specific embodiments of a motion-corrected image reconstruction process will be described.

First Embodiment

In the present embodiment, the filtering is performed based on a relation between indicators for noise amounts of the two images when the image pair is generated, and information including the presence or absence or a degree of the motion generated by the subject is acquired, and the information is reflected in the motion-corrected image reconstruction. In the present embodiment, a case will be described where, as the indicator for the noise amount, a tube current at the time when the transmitted X-ray data used for the generation of the image pair is acquired, is used.

Figure 4:
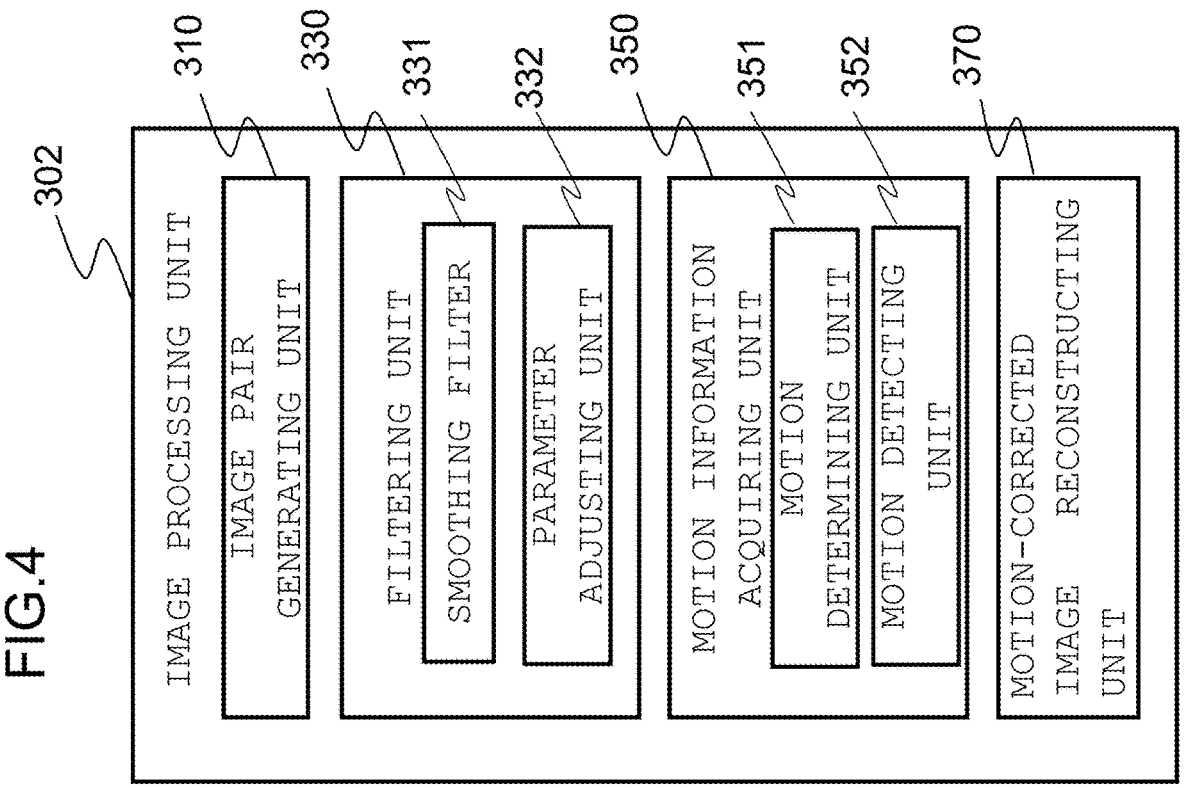
FIG. 4 is a functional block diagram of an image processing unit according to a first embodiment.

FIG. 4 illustrates a configuration example of the image processing unit 302 according to the present embodiment.

As illustrated, the image processing unit 302 includes an image pair generating unit 310, a filtering unit 330 that performs noise reduction, a motion information acquiring unit 350, and a motion-corrected image reconstructing unit 370. The filtering unit 330 includes a smoothing filter 331 and a parameter adjusting unit 332 that adjusts a smoothing parameter of a filter. A filter such as a low-pass filter, a high-pass filter, a Gaussian filter, or a bilateral filter can be used for smoothing, and the filtering unit 330 performs the noise reduction using one or more of these filters as the smoothing filter. The motion information acquiring unit 350 includes a motion determining unit 351 that determines the presence or absence of a motion, and a motion detecting unit 352 that detects a magnitude and a direction of a motion.

Hereinafter, the details of the motion-corrected image reconstruction process to be performed by the units of the image processing unit 302 will be described with reference to FIGS. 3B and 5.

First, a process (S31) of generating an image pair is performed.

Step S51

Based on the transmitted X-ray data collected by the data collection device 106 in the imaging step S1 (FIG. 3A), the image pair generating unit 310 generates two images, that is, a first image and a second image by filtered back projection. The two images constitute an image pair that directly face each other with the target image reconstruction position as a center.

Figure 6:
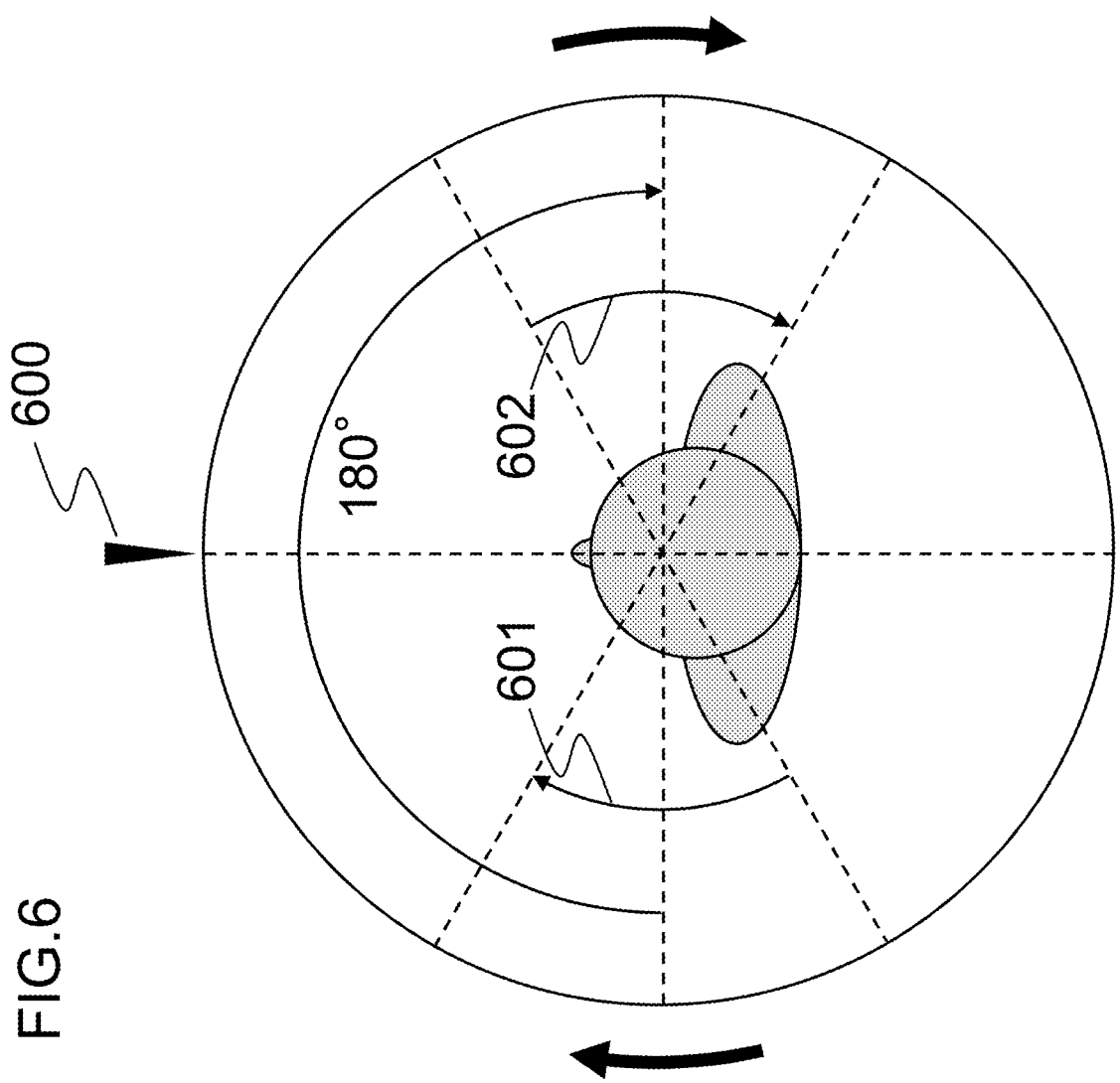
FIG. 6 is a diagram illustrating a relation between a first image and a second image with respect to a target reconstruction position.

FIG. 6 illustrates a relation between the target image reconstruction position, and the first image and the second image. In FIG. 6, a position 600 indicates a target image reconstruction center position set in the reconstruction condition setting step S2, and in this example, a position (a position of a rotation angle 0° of the scanner) where the X-ray tube and the subject 3 directly face each other is the target image reconstruction center position. Transmitted X-ray data in a predetermined angle range with the position 600 (0°) as a center, for example, in a range of 180° or more is used for reconstruction of a tomographic image, and an image pair is generated using transmitted X-ray data in ranges 601 and 602 that respectively use positions of −90° and +90° as centers and that are set as image reconstruction ranges. That is, the image reconstruction ranges 601 and 602 are equal to each other in size and are angle ranges of less than 180°, and the image reconstruction center positions thereof are separated from each other by 180°. A value specified as a default and may be set for the angle ranges, a setting/change by the user in the reconstruction condition setting step S2 may be accepted.

Each of the first image and the second image is not limited to a single two-dimensional image, and is a three-dimensional image includes a plurality of two-dimensional images.

Step S52

This step is a process for obtaining smoothness according to degrees of noises when the first image and the second image are subjected to the noise reduction by filtering, and first, the parameter adjusting unit 332 acquires tube currents serving as the indicators for the degrees of noises (the noise amounts).

Specifically, tube current information is acquired based on the transmitted X-ray data collected in the imaging step S1. The imaging may be performed by setting the tube current to be constant, and the tube current may be changed depending on the imaging condition. For example, in order to limit an exposure dose in imaging of the heart, tube currents may be changed, based on electrocardiogram waveform data at the time of the imaging, depending on a cardiac phase, i.e., a static phase where a reconstructed image is created or other phases.

Figure 7A:
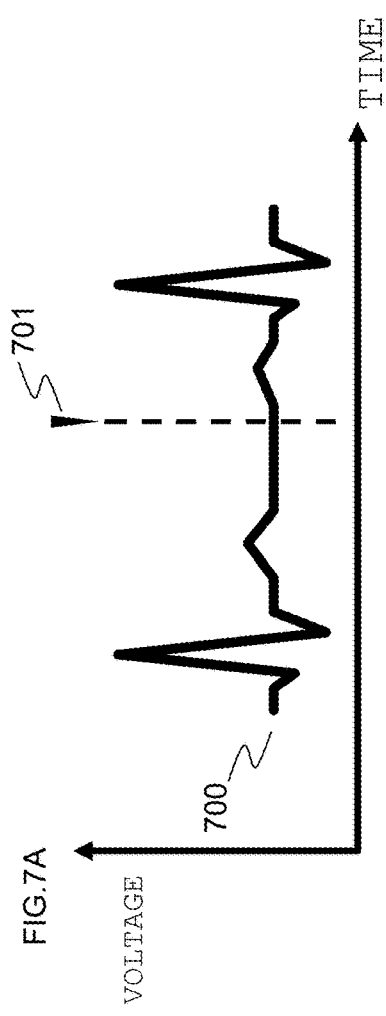
FIG. 7A is a graph illustrating a relation between electrocardiogram waveform data and a magnitude of a tube current value in electrocardiogram gated imaging, and is a graph illustrating an electrocardiogram waveform and a target imaging cardiac phase.
Figure 7B:
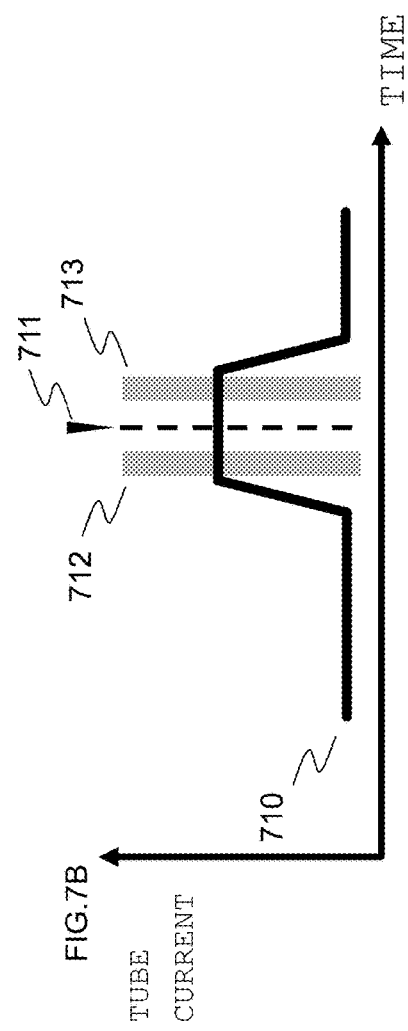
FIG. 7B is a graph illustrating a relation between the electrocardiogram waveform data and the magnitude of the tube current value in the electrocardiogram gated imaging, and is a graph illustrating a relation between the imaging cardiac phase and a tube current.
Figure 7C:
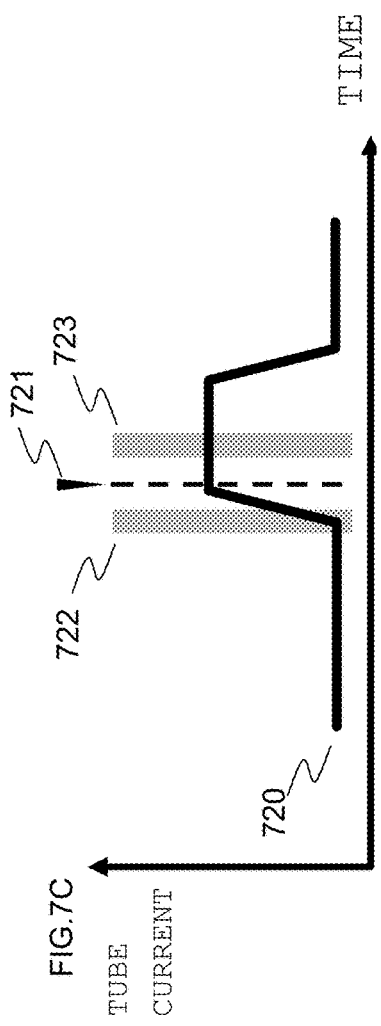
FIG. 7C is a graph illustrating a relation between the electrocardiogram waveform data and the magnitude of the tube current value in the electrocardiogram gated imaging, and is a graph illustrating a relation between the imaging cardiac phase and the tube current.

FIGS. 7A to 7C illustrate examples of a relation between the electrocardiogram waveform data (700) and the magnitude of tube current values (710 and 720) when the tube currents are changed. When an imaging target cardiac phase 701 is set between n adjacent R waves in an electrocardiogram 700 illustrated in FIG. 7A, the tube current is set such that a center of the waveform is set to be the imaging target cardiac phase 701 as illustrated in FIG. 7B.

Here, when a cardiac phase to be selected at the time of reconstruction (that is, the target image reconstruction position) 711 set in the condition setting step S2 matches with the imaging target cardiac phase 701, tube current values in an image reconstruction range 712 for the first image and an image reconstruction range 713 for the second image at equal distances (equal time intervals) to the position 711 become equal. However, as illustrated in FIG. 7C, when a cardiac phase to be selected at the time of reconstruction (the target image reconstruction position) 721 is deviated to a certain extent from the imaging target cardiac phase 701, a tube current value in an image reconstruction range 722 for the first image does not match with a tube current value in an image reconstruction range 723 for the second image.

Since the transmitted X-ray data includes information on the tube current at the time of acquisition as additional information, the parameter adjusting unit 332 calculates, using the information on the tube current at the time of acquiring the first image and the second image, respective average tube current values and an average tube current ratio, for the first image and the second image that are acquired in the image pair generation step S51. The average tube current value is an average value of the tube currents varying in each of the image reconstruction ranges 601 and 602 illustrated in FIG. 6, and the average tube current ratio is a value (or the reciprocal thereof) obtained by dividing the average tube current value of the first image by the average tube current value of the second image.

Step S53

The parameter adjusting unit 332 determines, using the average tube current values and the average tube current ratio of the first image and the second image that are acquired in the tube current acquisition step S52, a smoothing parameter of a filter to be used in a subsequent filtering process S54.

Specifically, when the average tube current ratio of the first image and the second image is within a certain range around 1, for example, when the electrocardiographic phase 700 (the target imaging cardiac phase 701) and a tube current 710 are in the relation as illustrated in FIG. 7B, the same smoothing parameter is set for the first image and the second image based on information on the average tube current values. For example, the certain range can be determined in advance such that, for example, the average tube current ratio is within a range of 0.9 to 1.1.

On the other hand, when the average tube current ratio of the first image and the second image is outside the certain range around 1, for example, when the electrocardiographic phase 700 (the target imaging cardiac phase 701) and a tube current 720 are in the relation as illustrated in FIG. 7C, the same smoothing parameter or different smoothing parameters are set for the first image and the second image based on information on one or more of the average tube current values and the average tube current ratio.

Figure 8A:
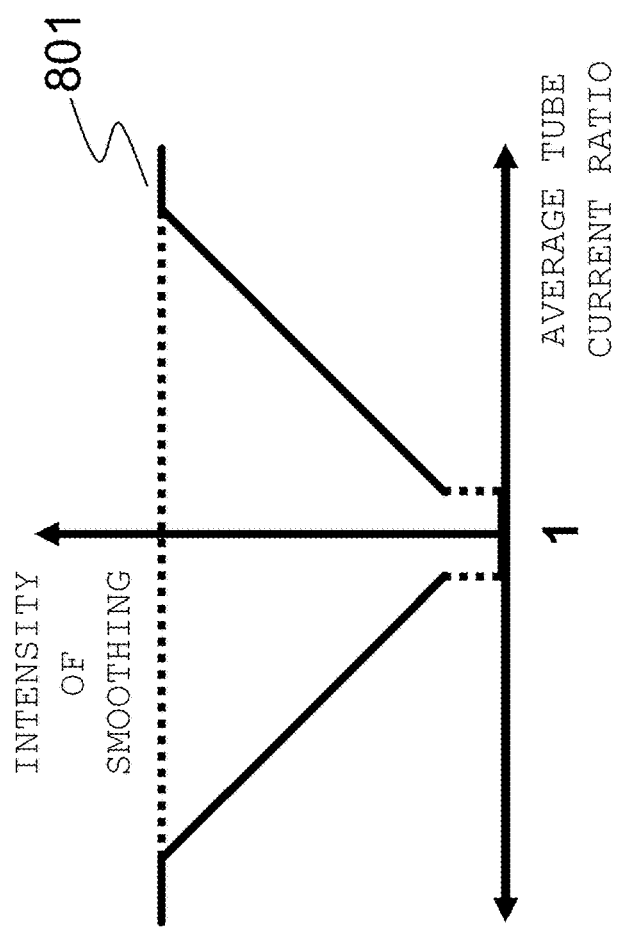
FIG. 8A is a graph illustrating a smoothing parameter adjustment method based on a relation between tube current values according to the first embodiment, and is a graph illustrating an adjustment using an average tube current value.
Figure 8B:
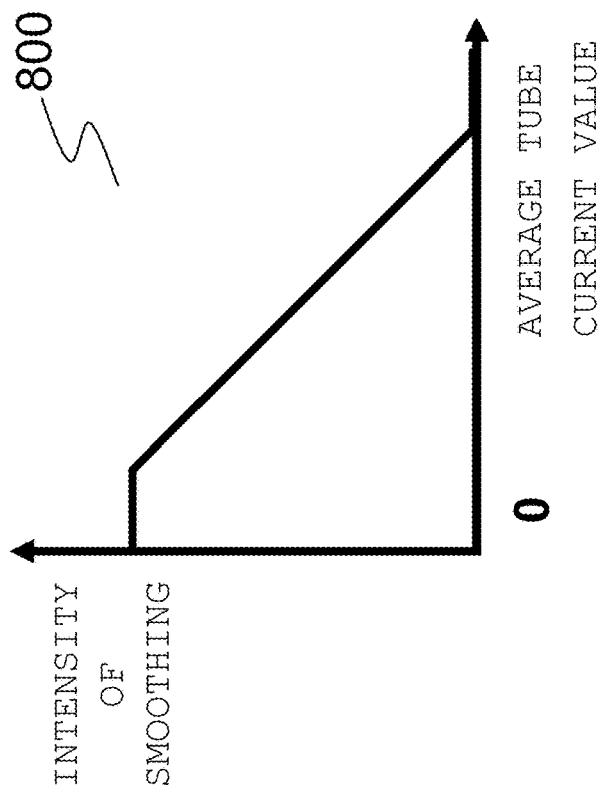
FIG. 8B is a graph illustrating the smoothing parameter adjustment method based on the relation between the tube current values according to the first embodiment, and is a graph illustrating an adjustment using an average tube current ratio.

FIGS. 8A and 8B illustrate a case where the parameter is adjusted based on the average tube current values and a case where the parameter is adjusted based on the information on the average tube current ratio. As illustrated in FIG. 8A, when average tube current values 800 of the first image and the second image are used, the smoothing parameter is adjusted toward a direction where the smoothing is weakened as the values increase. That is, the noise is decreased as the average tube current values become large, and the noise is increased as the average tube current values become small. Therefore, when the average tube current values of the first image and the second image are different, the smoothness of the image having a larger average tube current value is weakened, and the smoothness of the image having a smaller average tube current value is strengthened.

As illustrated in FIG. 8B, when an average tube current ratio 801 of the first image and the second image is used, the smoothing parameter is adjusted toward a direction where smoothing for an image serving as a reference is strengthened as a value of the ratio increases from 1 toward an increasing direction, and the smoothing parameter is adjusted toward a direction where smoothing for an image other than the image serving as a reference is strengthened as the value of the ratio decreases from 1 toward a decreasing direction.

By using the average tube current values or the average tube current ratio in this way, it is possible to perform the noise reduction reflecting the relation of noise between the image pair. When either the average tube current values or the average tube current ratio of the first image and the second image is used, an upper limit value is set for the smoothing parameter. Accordingly, excessive smoothing can be prevented.

In FIGS. 8A and 8B, the average tube current values and intensity of the smoothing, and the average tube current ratio and the intensity of the smoothing have a linear correlation, and may have a nonlinear correlation.

In FIGS. 8A and 8B, the smoothing parameter to be adjusted is shown as "intensity of the smoothing" (a vertical axis) in a collective manner, and the smoothing parameter differs depending on a filter to be used. As an example, an adjustable parameter in a case of using a bilateral filter will be described.

The bilateral filter is represented by the following Equation (1), and three parameters w, $\sigma_1$, and $\sigma_2$ in the equation are parameters for determining the intensity of the smoothing, and the intensity of the smoothing is determined by adjusting one or more of these parameters. When the intensity of the smoothing is increased, values of w, $\sigma_1$, and $\sigma_2$ are adjusted to be increased, and when the intensity of the smoothing is decreased, the values of w, $\sigma_1$, and $\sigma_2$ are adjusted to be decreased.

$$g(i,j) = \frac{\sum_{n=-w}^{w}\sum_{m=-w}^{w} f(i+m, j+n)\exp\left(-\frac{m^2+n^2}{2\sigma_1^2}\right) \exp\left(-\frac{(f(i,j)-f(i+m,j+n))^2}{2\sigma_2^2}\right)}{\sum_{n=-w}^{w}\sum_{m=-w}^{w} \exp\left(-\frac{m^2+n^2}{2\sigma_1^2}\right) \exp\left(-\frac{(f(i,j)-f(i+m,j+n))^2}{2\sigma_2^2}\right)} \quad (1)$$

In the equation, f (i, j) represents an array of input image data, g (i, j) represents an array of output image data, w represents a size of a kernel, $\sigma_1$ represents a weight in consideration of a distance to a target voxel, and $\sigma_2$ represents a weight in consideration of a difference in pixel value from the target voxel.

Step S54

In this step, the filter having the parameter set by the parameter adjusting unit 332 is applied to the first image and the second image that are acquired in the image pair generation step S51, and the first image and second image after filtering are acquired.

FIG. 9 illustrates a result of the filtering process performed for the first image and the second image that have average tube current values significantly different from each other. As illustrated, a first image 900 and a second image 901 before the filtering significantly differ from each other in a tendency of noise due to a large difference between the average tube current values. However, by performing filtering of parameters optimized for the first image and the second image, tendencies of noise of a first image 910 and a second image 911 after the filtering are close to each other.

The image pair generation step S31 in FIG. 3B is completed by the above steps S51 to S54.

Subsequently, the motion is detected using the image after the filtering (the motion information pair acquisition step S32). In the motion information acquisition step S32, prior to the detection of the motion, the presence or absence of the motion is determined using a difference between the two images. The details thereof will be described below.

Step S55

In this step, first, an image difference is acquired for the first image and the second image that are acquired in S51 or the first image and the second image after the filtering in S54. As described in S51, the first image and the second image are generated for each of a plurality of cross sections in the case of the three-dimensional image. That is, a plurality of image pairs are acquired, and a plurality of difference images are also acquired. Regarding all the acquired difference images, a standard deviation in a pixel value is calculated for each image, and a median value of the standard deviations of all the difference images is set as a representative value of the standard deviation for the image pairs. That is, the representative value of the standard deviation is an indicator for the motion of the acquired three-dimensional images as a whole.

Step S56

The presence or absence of the motion of the subject is determined based on the value of the standard deviation acquired in the standard deviation calculation step S55 described above. Specifically, when the value of the standard deviation is equal to or larger than a threshold value, it is determined that there is a motion in the subject, and when the value of the standard deviation is less than the threshold value, it is determined that there is no motion in the subject.

Figure 10:
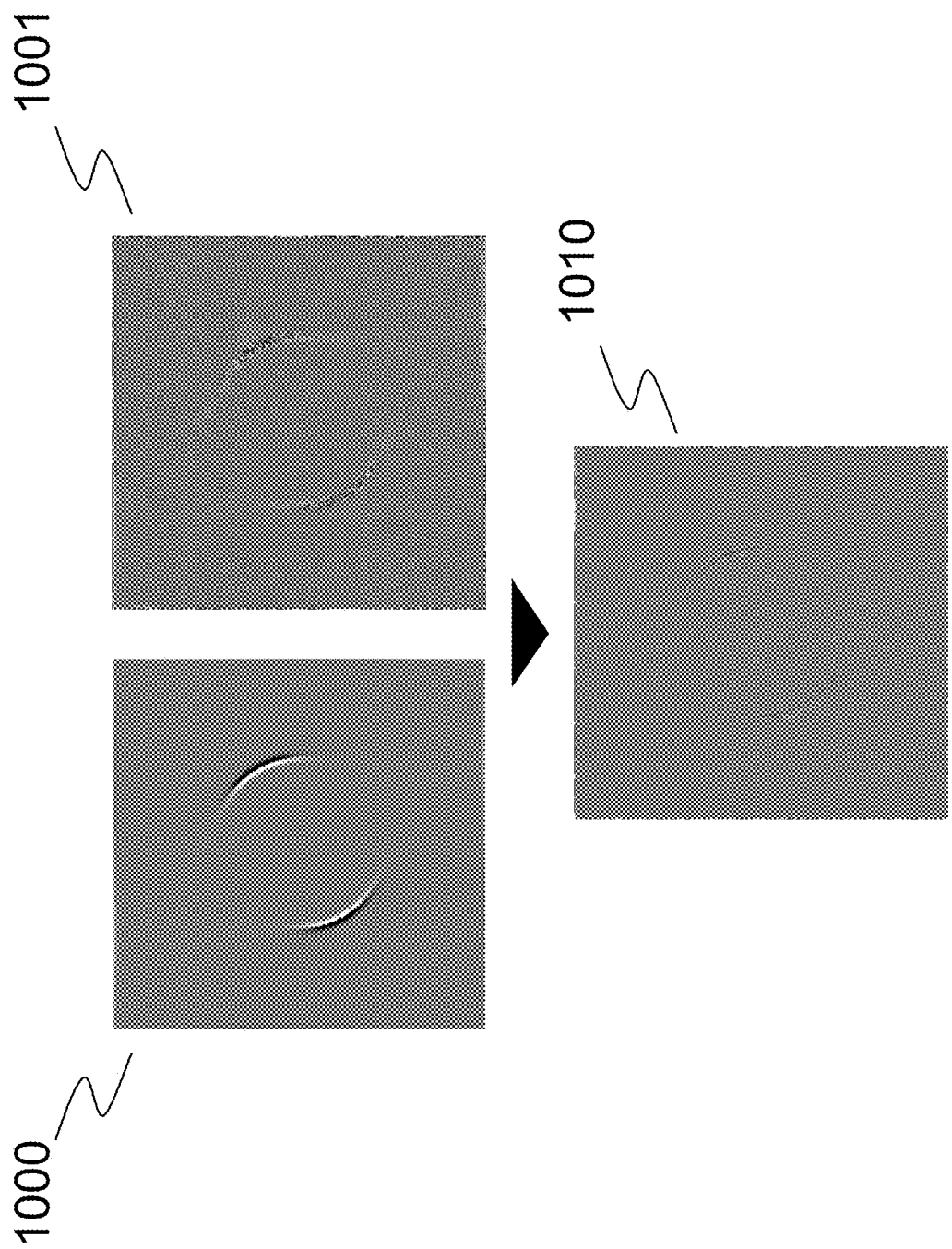
FIG. 10 is a functional block diagram of an image processing unit according to a second embodiment.

FIG. 10 illustrates a determination example of the presence or absence of a motion for a subject having no motion. In FIG. 10, a difference image 1010 is a difference image of a first image 1000 and a second image 1001 after the filtering. As illustrated, the difference image 1010 has a low pixel value, and the value of the standard deviation calculated therefrom is less than the threshold value. Therefore, it is determined that there is no motion in the subject.

Step S57

Based on a result of the determination of the presence or absence of the motion (S56), a normalization process for the pixel value is performed for the first image and the second image after the filtering. All pixels of the first image and the second image are normalized by, for example, Min-Max method, and different processes are performed according to the determined result in the determination step S56.

Regarding an image in which it is determined that there is a motion in the subject, the image is normalized in a range of a minimum value 0 to a maximum value 1 by applying Equation (2) to an input image.

Regarding an image in which it is determined that there is no motion in the subject, the image is normalized in a range of the minimum value 0 to a maximum value M (0<M≤1) by applying an equation, which is acquired by increasing a denominator ($f_{max}-f_{min}$) of Equation (2) to a predetermined constant value T (T≥$f_{max}-f_{min}$), to the input image.

$$g(i, j) = \frac{f(i, j) - f_{min}}{f_{max} - f_{min}} \qquad (2)$$

f(i, j): the array of the input image data
g(i, j): the array of the output image data
$f_{min}$: the minimum value of the pixel value of the input image
$f_{max}$: the maximum value of the pixel value of the input image By determining the presence or absence of the motion in this way, and changing a method for normalization based on a determined result thereof (that is, adjusting a value after the normalization when there is no motion to be small in advance), an intensity of motion correction is adjusted. Accordingly, it is possible to prevent excessive motion correction even when there is no motion.

Step S58

After the above steps S55 to S57 are completed, the motion is detected using the normalized image pair (S32 in FIG. 3B). This process is the same as that of a motion detection technique in the related art, and non-rigid registration of the two images is performed to calculate a motion vector between the images.

Step S59

Finally, the image reconstructing unit 301 performs the image reconstruction using the motion vector acquired in step S58 and the transmitted X-ray data collected in the imaging step (FIG. 3A: S1).

Regarding the motion-corrected image reconstruction, a tomographic image can be reconstructed by estimating, based on the motion vector that is calculated based on the first image and the second image created at positions separated from each other by 180° with the target reconstruction positions as centers, a magnitude and a direction of the motion of the subject at the time of acquiring the transmitted X-ray data used for the image reconstruction, and performing back projection while correcting the images of the target reconstruction positions based on this information.

By performing this process for each of the plurality of cross sections, 3D tomographic image data subjected to the motion correction can be acquired. The acquired tomographic image is stored in the storage device 213 and is displayed on the display device 211 as necessary.

As described above, according to the present embodiment, by performing the noise reduction reflecting the relation between the tube currents when each image of the image pair for detecting the motion is acquired, it is possible to prevent a problem that a difference in noise between the two images is erroneously recognized as a motion component and to prevent loss in the motion component due to excessive smoothing, and it is possible to improve the accuracy of the motion correction.

Further, according to the present embodiment, even if the tube current values of the first image and the second image are unknown at the time of setting the image reconstruction condition, the tube current values are acquired from the additional information of the transmitted X-ray data, and the tube current values are reflected in the noise reduction. Therefore, even when the tube current values vary, the noise reduction corresponding to variations can be performed, and it is possible to prevent a deterioration in the accuracy of the motion correction and to reduce the unnatural distortion of the image.

Further, according to the present embodiment, by determining the presence or absence of the motion of the subject, and changing a condition at the time of normalizing the two images according to a degree (the presence or absence) of the motion, it is possible to solve problems such as execution of the excessive correction even in a case where the motion is minute and occurrence of the unnatural distortion due to the image noise.

Although the present embodiment is an example in which (1) the noise reduction reflecting the relation between the tube currents and (2) the motion correction reflecting the determined result on the presence or absence of the motion of the subject are performed in combination, implementation of only one of the two ways is also included in the invention.

Second Embodiment

In the first embodiment, the target image reconstruction position (the reconstruction cardiac phase) is set in the image reconstruction condition setting step S2. Accordingly, the positions of the image pair used for the motion correction are determined. Therefore, the noise reduction process is performed using the tube current values of the first image and the second image that are actually acquired.

On the other hand, in the present embodiment, in the image pair generation step (FIG. 3: S31), a range (a motion-correctable range) is acquired in which the motion correction can be appropriately performed, and the reconstruction cardiac phase is set in this range. Accordingly, a risk of the deterioration in the accuracy of the motion correction and the occurrence of the unnatural distortion is reduced in advance.

Figure 11:
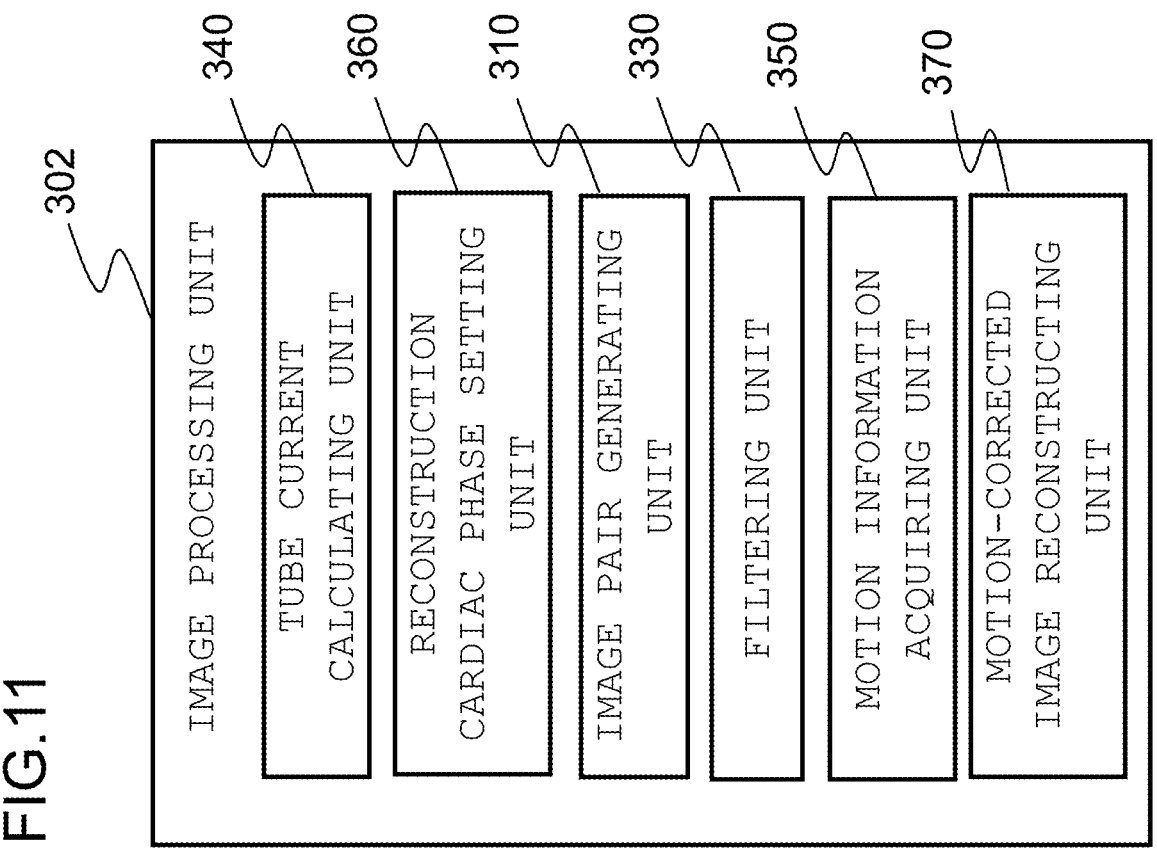
FIG. 11 is a diagram illustrating a flow of a process for setting an image reconstruction condition according to the second embodiment.

In the present embodiment, the configuration of the image processing unit 302 is the same as that according to the first embodiment illustrated in FIG. 4. As illustrated in FIG. 11, a tube current calculating unit 340 and a reconstruction cardiac phase setting unit (a cardiac phase setting unit) 360 are added. The tube current calculating unit 340 may be provided in common with the parameter adjusting unit 332 according to the first embodiment that calculates the tube currents.

Figure 12:
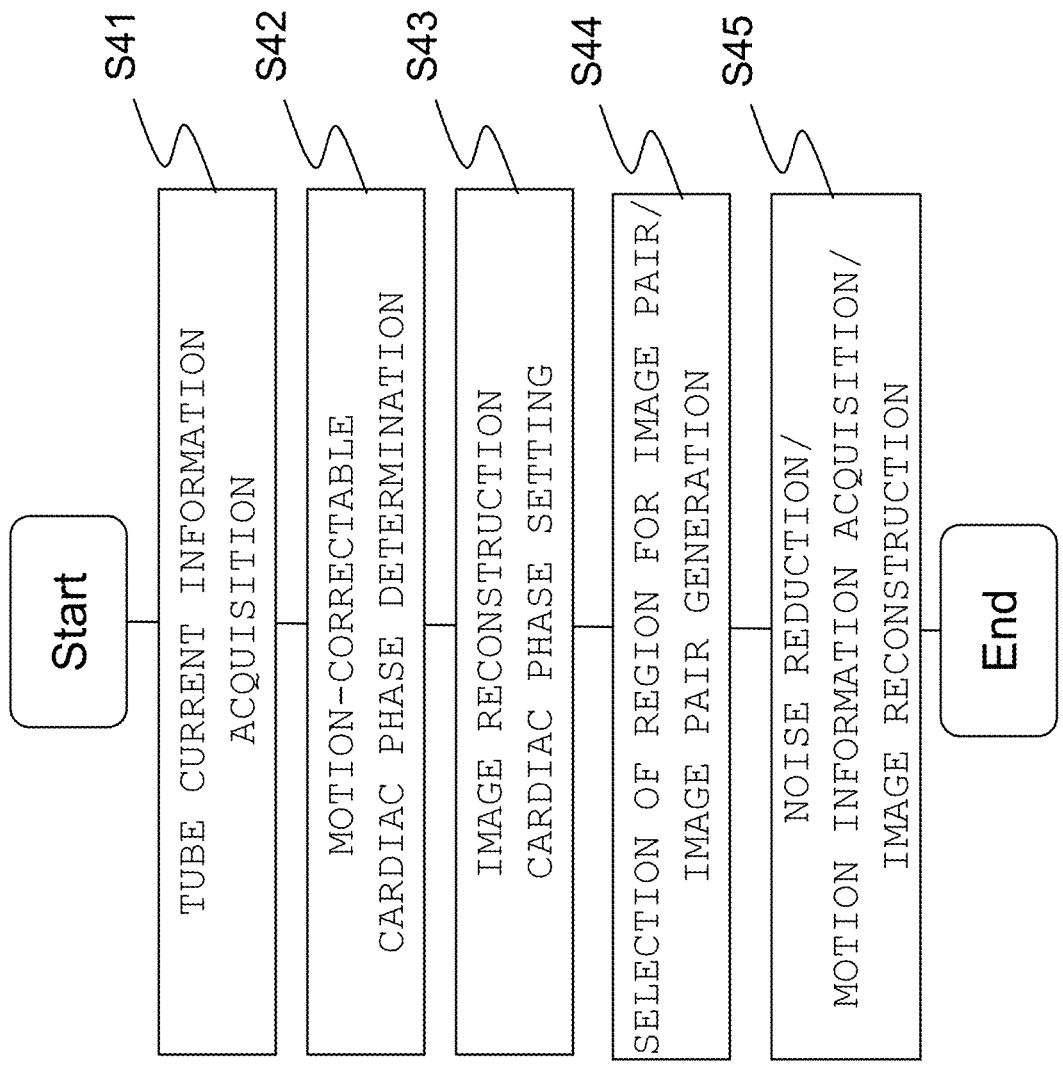
FIG. 12 is a diagram illustrating a display example for setting the image reconstruction condition according to the second embodiment.

Hereinafter, a flow of processes according to the present embodiment will be described with reference to FIG. 12.

Step S41

The tube current calculating unit 340 acquires the tube current information based on the transmitted X-ray data collected in the imaging step S1. The tube current information is acquired as a graph of the tube current as illustrated in FIG. 7A, and here, the tube current is supplied in a manner of becoming High within a predetermined phase range including an imaging target cardiac phase.

By using the tube current information, the tube current calculating unit 340 calculates average tube current values of two images directly facing each other in the predetermined cardiac phase range, at every regular interval of the cardiac phase. Further, an average tube current ratio of the two images may be calculated. The average tube current values and the average tube current ratio are the same as those acquired in the tube current acquisition step S52 according to the first embodiment.

Step S42

Next, the reconstruction cardiac phase setting unit 360 predicts whether a certain effect can be attained by correcting the motion using at least one of the average tube current values and the average tube current ratio that are calculated by the tube current calculating unit 340. Specifically, for example, when average tube current values of an image pair in a cardiac phase range are equal to or larger than a preset threshold value, the cardiac phase range (the cardiac phase) is determined as a motion-correctable cardiac phase. When the average tube current values are smaller than the threshold value, the cardiac phase is determined as a motion-uncorrectable cardiac phase. Such a determination is performed while shifting the cardiac phase range at predetermined intervals, and finally, it is determined whether the motion correction is possible for the entire range of the acquired transmitted X-ray data. In a case of using the average tube current ratio as well, it is determined that the motion correction is possible or impossible depending on whether a value of the average tube current ratio is close to 1 (for example, whether the average tube current ratio is within the range of 0.9 to 1.1).

Figure 13:
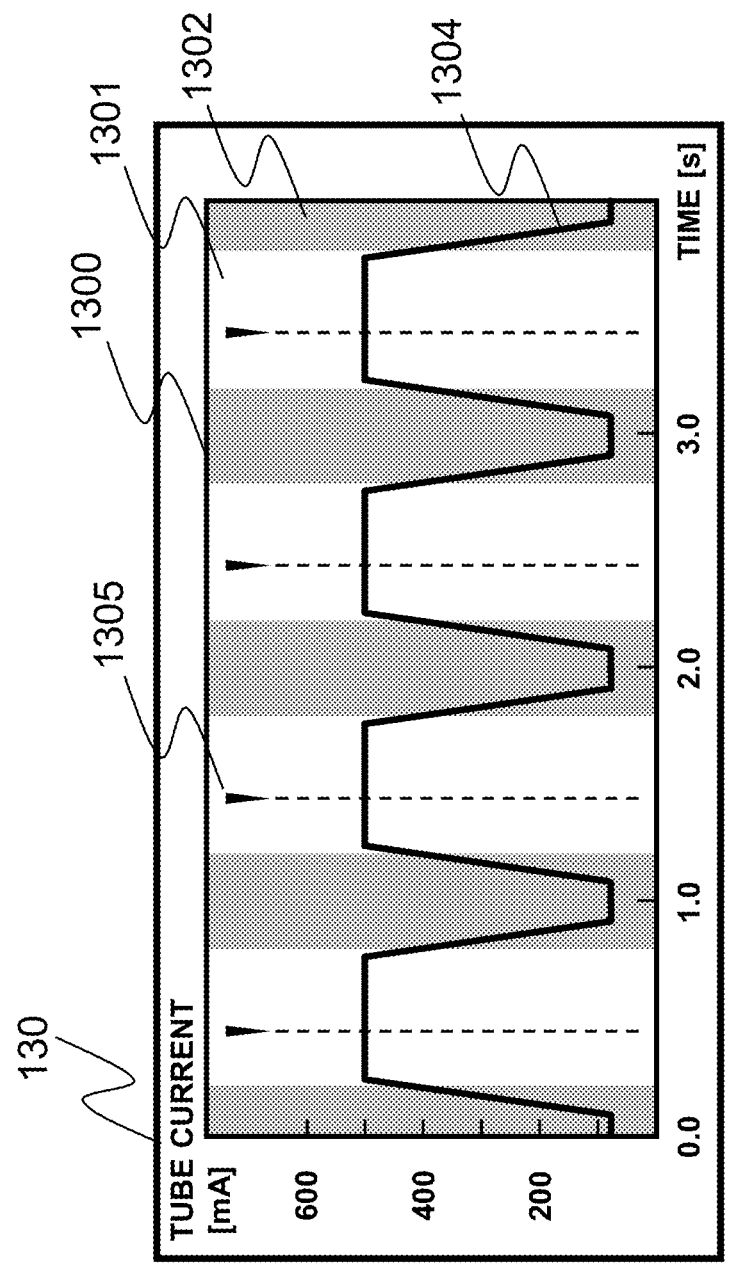
FIG. 13 is a diagram illustrating setting of a reconstruction cardiac phase position.

An example of a result acquired by such a determination is illustrated in FIG. 13. In FIG. 13, in a region 1300 where the reconstruction cardiac phase is to be set, a region 1301 indicated in white is a region where the motion correction is determined to be possible, and a region 1302 indicated in gray is a region where the motion correction is determined to be impossible. Each of the regions corresponds to a region of the cardiac phase.

Step S43

The reconstruction cardiac phase setting unit 360 determines the reconstruction cardiac phase (the image reconstruction position) based on a determined result of the determination step S42, and sets the reconstruction cardiac phase as the reconstruction condition (FIG. 3A: S2). This determination of the reconstruction cardiac phase may be automatically performed based on the determined result, and the reconstruction cardiac phase may be set at any position by displaying a screen 130 including a tube current value 1304, a motion-correctable region 1301, and a motion-uncorrectable region 1302, and a mark (GUI) 1305 indicating a reconstruction cardiac phase as illustrated in FIG. 13 on the display device 211, and operating the mark 1305 by the user at the time of setting the reconstruction condition. On this display screen, an electrocardiographic image and an electrocardiographic waveform that are acquired at the same time of the imaging may be displayed with time axes thereof aligned. Accordingly, the user can specify an appropriate reconstruction cardiac phase even when the imaging target cardiac phase and the tube current are deviated.

Step S44

The image pair generating unit 310 generates a first image and a second image by selecting a region for the first image and a region for the second image as illustrated in FIG. 6 based on the set reconstruction cardiac phase (the image reconstruction position).

Step S45

Figure 5:
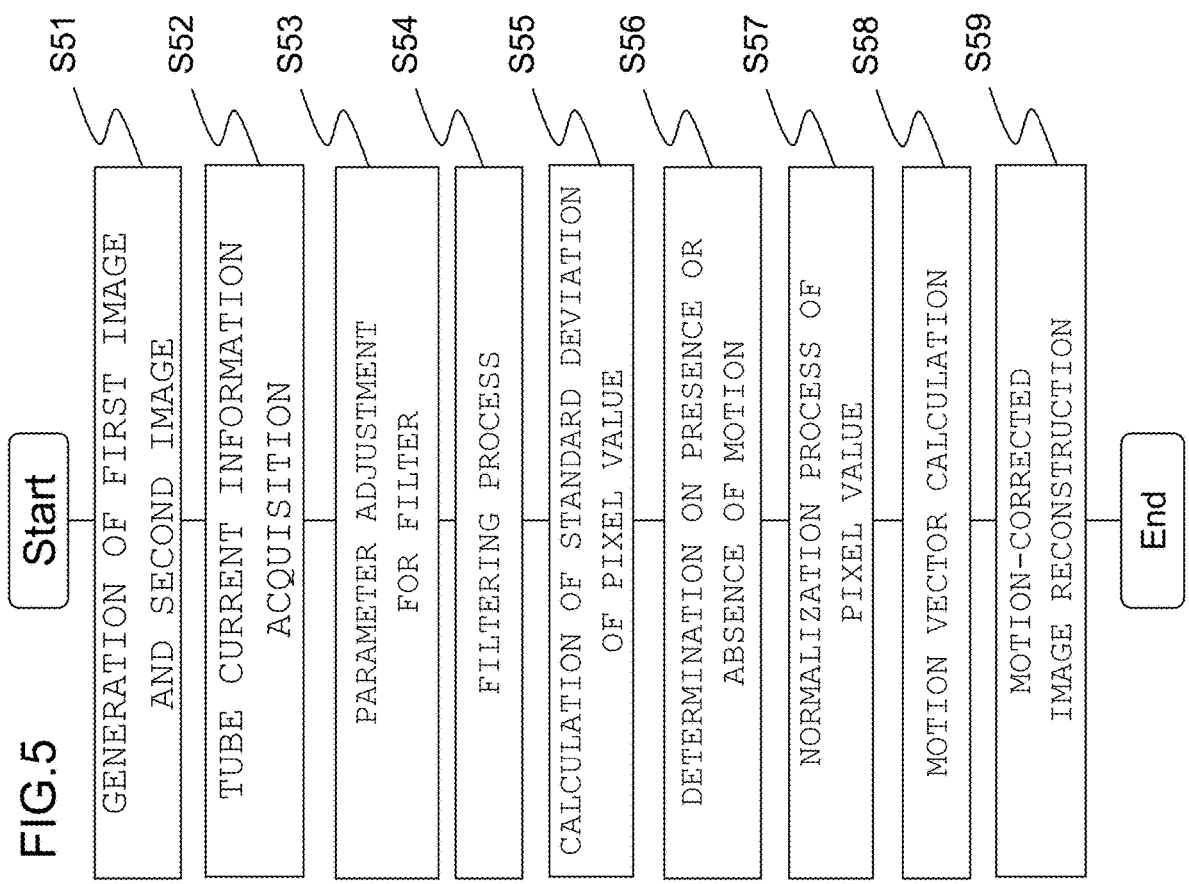
FIG. 5 is a diagram illustrating a flow of a motion-corrected image reconstruction process according to the first embodiment.

Processes after the generation of the image pair are the same as those according to the first embodiment illustrated in FIG. 5, and the parameter adjustment for the filter (S53), the filtering process (S54), the calculation of the standard deviation of the pixel value (S55), the determination on the presence or absence of the motion (S56), the normalization of the pixel value (S57), the motion vector calculation (S58), and the like are performed. However, regarding the acquisition of the tube current information (S52) included in the processes in FIG. 5, since the average tube current values or the average tube current ratio is calculated in step S41 described above, the value calculated for the image pair used for motion detection can be used, and this process can be omitted.

According to the present embodiment, it is possible to optimize the image pair used for the motion correction at a stage of setting the reconstruction condition, and it is possible to improve practical effectiveness of the motion correction.

In the above embodiments, the tube current values are used as the indicators for the noise amounts, and further, information that affects a tendency of a noise difference between the image pair can be used. For example, the indicators for the noise amounts at the time of acquiring the transmitted X-ray data can be calculated using a value of a tube voltage in the same manner as the tube current. In addition, the tendency of the noise changes depending on a reconstruction method, a reconstruction filter function, a detector array, or the like, and thus one or more of the above may be added to calculate the indicators for the noise amounts. Here, the reconstruction method is filtered back projection or iterative reconstruction. The reconstruction filter function includes filter functions different for the heart, the lung field, the head, and the like. The detector array is the number of columns (16 columns, 64 columns, 256 columns, or the like) of detectors.

What is claimed is:

1. An X-ray CT apparatus comprising:
    an imaging unit provided with an X-ray source and an X-ray detector which rotate around a subject, and configured to acquire transmitted X-ray data of the subject in a predetermined angle range;
    an image reconstructing unit configured to generate a reconstructed image using the transmitted X-ray data acquired by the imaging unit; and
    an image processing unit including
        an image pair generating unit configured to generate an image pair at positions directly facing each other using a part of the transmitted X-ray data,
        a noise reducing unit configured to perform noise reduction for each image of the image pair generated by the image pair generating unit, and
        a motion information acquiring unit configured to acquire motion information of the subject during scanning using the image pair after the noise reduction, wherein
    the noise reducing unit performs, based on a relation between indicators for noise amounts of the images included in the image pair, the noise reduction for each image of the image pair, the indicators for the noise amounts being tube currents at a time of acquiring the transmitted X-ray data used for generation of the image pair, and the relation between the indicators being at least one of average tube current values and a ratio of the average tube current values at a time of acquiring image data of the image pair, and
    the image reconstructing unit generates a reconstructed image by correcting a motion of the subject during scanning using the motion information calculated by the motion information acquiring unit.

2. An X-ray CT apparatus comprising:
    an imaging unit provided with an X-ray source and an X-ray detector which rotate around a subject, and configured to acquire transmitted X-ray data of the subject in a predetermined angle range;
    an image reconstructing unit configured to generate a reconstructed image using the transmitted X-ray data acquired by the imaging unit; and
    an image processing unit including
        an image pair generating unit configured to generate an image pair at positions directly facing each other using a part of the transmitted X-ray data,
        a noise reducing unit configured to perform noise reduction for each image of the image pair generated by the image pair generating unit, and
        a motion information acquiring unit configured to acquire motion information of the subject during scanning using the image pair after the noise reduction, wherein
    the noise reducing unit performs, based on a relation between indicators for noise amounts of the images included in the image pair, the noise reduction for each image of the image pair,
    the image reconstructing unit generates a reconstructed image by correcting a motion of the subject during scanning using the motion information calculated by the motion information acquiring unit,
    the noise reducing unit includes a filter and a parameter adjusting unit configured to adjust a smoothing parameter of the filter, and
    the parameter adjusting unit adjusts the parameter based on at least one of average tube current values and a ratio of the average tube current values at a time of acquiring image data of the image pair.

3. The X-ray CT apparatus according to claim 2, wherein the parameter adjusting unit adjusts a smoothness of an image having a small average tube current value to be higher than a smoothness of an image having a large average tube current value at the time of acquiring the image data.

4. An X-ray CT apparatus comprising:
    an imaging unit provided with an X-ray source and an X-ray detector which rotate around a subject, and configured to acquire transmitted X-ray data of the subject in a predetermined angle range;
    an image reconstructing unit configured to generate a reconstructed image using the transmitted X-ray data acquired by the imaging unit; and
    an image processing unit including
        an image pair generating unit configured to generate an image pair at positions directly facing each other using a part of the transmitted X-ray data,
        a noise reducing unit configured to perform noise reduction for each image of the image pair generated by the image pair generating unit, and
        a motion information acquiring unit configured to acquire motion information of the subject during scanning using the image pair after the noise reduction, wherein
    the noise reducing unit performs, based on a relation between indicators for noise amounts of the images included in the image pair, the noise reduction for each image of the image pair,
    the image reconstructing unit generates a reconstructed image by correcting a motion of the subject during scanning using the motion information calculated by the motion information acquiring unit, and the motion information acquiring unit includes a motion determining unit configured to determine presence or absence of a motion using the image pair after the noise reduction, and performs a normalization process for each image of the image pair based on a result of the motion determining unit.

5. The X-ray CT apparatus according to claim 4, wherein the motion determining unit calculates difference images for a plurality of the image pairs, and determines the presence or absence of a motion using a standard deviation of a pixel value of each of the difference images.

6. An X-ray CT apparatus comprising:
an imaging unit provided with an X-ray source and an X-ray detector which rotate around a subject, and configured to acquire transmitted X-ray data of the subject in a predetermined angle range;
an image reconstructing unit configured to generate a reconstructed image using the transmitted X-ray data acquired by the imaging unit;
an image processing unit including
an image pair generating unit configured to generate an image pair at positions directly facing each other using a part of the transmitted X-ray data,
a noise reducing unit configured to perform noise reduction for each image of the image pair generated by the image pair generating unit, and
a motion information acquiring unit configured to acquire motion information of the subject during scanning using the image pair after the noise reduction; and
a cardiac phase setting unit configured to set a reconstruction cardiac phase at a time of electrocardiogram gated imaging, wherein
the noise reducing unit performs, based on a relation between indicators for noise amounts of the images included in the image pair, the noise reduction for each image of the image pair,
the image reconstructing unit generates a reconstructed image by correcting a motion of the subject during scanning using the motion information calculated by the motion information acquiring unit, and
the cardiac phase setting unit calculates, over a plurality of cardiac phase ranges, at least one of average tube current values and an average tube current ratio of the images in the image pair generated based on the transmitted X-ray data, and determines a motion-correctable cardiac phase region for a cardiac phase range calculated using a calculated result.

7. The X-ray CT apparatus according to claim 6, wherein the cardiac phase setting unit sets the reconstruction cardiac phase in the determined motion-correctable cardiac phase region.

8. The X-ray CT apparatus according to claim 6, wherein the cardiac phase setting unit displays the determined motion-correctable cardiac phase region on a display device, and receives a setting for the reconstruction cardiac phase performed by a user.

9. An image processing apparatus for receiving transmitted X-ray data collected by an X-ray CT apparatus and performing motion-corrected image reconstruction, the image processing apparatus comprising:
an image pair generating unit configured to generate an image pair at positions directly facing each other using a part of the transmitted X-ray data;
a noise reducing unit configured to perform noise reduction for each image of the image pair generated by the image pair generating unit, with a smoothness adjusted based on a relation between indicators for noise amounts of the images included in the image pair;
a motion information acquiring unit configured to acquire motion information of a subject during scanning, using the image pair after the noise reduction; and
an image reconstructing unit configured to generate a CT image in which a motion of the subject during scanning is corrected using the motion information calculated by the motion information acquiring unit,
wherein the indicators for the noise amounts include tube currents at a time of acquiring the transmitted X-ray data used for generation of the image pair, and the relation between the indicators includes at least one of average tube current values and a ratio of the average tube current values at a time of acquiring image data of the image pair.

10. A motion-corrected image reconstruction method for reconstructing a CT image by correcting a motion of a subject during scanning using transmitted X-ray data, the method comprising:
generating an image pair using a part of the transmitted X-ray data;
performing noise reduction for each image of the image pair, and at that time, adjusting, based on a relation between indicators for noise amounts of the images included in the image pair, filtering smoothness at a time of the noise reduction;
acquiring motion information of the subject from the image pair after the noise reduction; and
reconstructing an image using the motion information and the transmitted X-ray data,
the indicators for the noise amounts being tube currents at a time of acquiring the transmitted X-ray data used for generation of the image pair, and the relation between the indicators being at least one of average tube current values and a ratio of the average tube current values at a time of acquiring image data of the image pair.

11. A motion-corrected image reconstruction method for reconstructing a CT image by correcting a motion of a subject during scanning using transmitted X-ray data, the method comprising:
generating an image pair using a part of the transmitted X-ray data;
performing noise reduction for each image of the image pair, and at that time, adjusting, based on a relation between indicators for noise amounts of the images included in the image pair, filtering smoothness at a time of the noise reduction;
acquiring motion information of the subject from the image pair after the noise reduction;
reconstructing an image using the motion information and the transmitted X-ray data;
generating a difference image of the image pair after the noise reduction, and determining presence or absence of the motion of the subject using a standard deviation of a pixel value of the difference image; and
performing a normalization process for the image pair based on a determined result.

* * * * *